United States Patent [19]
Tehrani

[11] Patent Number: 5,173,163
[45] Date of Patent: Dec. 22, 1992

[54] CAPILLARY ELECTROPHORESIS TECHNIQUE

[75] Inventor: Yoossef Tehrani, Lincoln, Nebr.

[73] Assignee: Isco, Inc., Lincoln, Nebr.

[21] Appl. No.: 463,357

[22] Filed: Jan. 11, 1990

[51] Int. Cl.$^5$ .................. G01N 27/26; B01D 57/02
[52] U.S. Cl. ........................ 204/299 R; 204/180.1
[58] Field of Search ................ 204/299 R, 180.1

[56] References Cited

U.S. PATENT DOCUMENTS

| | | | |
|---|---|---|---|
| 4,676,897 | 6/1987 | Kuze et al. | 204/299 R X |
| 4,898,658 | 2/1990 | Karger et al. | 204/180.1 X |
| 5,006,210 | 4/1991 | Yueng et al. | 204/180.1 |

Primary Examiner—John Niebling
Assistant Examiner—John S. Starsiak, Jr.
Attorney, Agent, or Firm—Vincent L. Carney

[57] ABSTRACT

To inject sample into an electrophoresis capillary tube having a separating medium, the end of the capillary tube is inserted in an injection block with a liquid tight seal and a syringe is inserted into the block to apply fluid to the end of the capillary tube. The injection block provides split flow injection. A high voltage isolated switching arrangement switches the end of the capillary from the injection block to buffer at a high electrical potential to accomplish the electrophoretic separation. A second injection block is used to purge the capillary tube and can be used to supply separating medium as needed.

41 Claims, 5 Drawing Sheets

CAPILLARY ELECTROPHORESIS TECHNIQUE

BACKGROUND OF THE INVENTION

This invention relates to capillary electrophoresis.

One class of capillary electrophoresis system includes as its principal parts: (1) a length of capillary tube filled with an appropriate buffer; (2) a sample injector for injecting a small quantity such as 1 to 30 nl (nanoliters) of sample mixture into one end of the length of capillary tube; (3) means for applying an electrical potential between the two ends of the length of capillary tube which potential is normally applied by a high-voltage, low-current power supply; and (4) an on-line detector. An example of this type of equipment is described in U.S. application Ser. No. 07/277,566 filed Nov. 29, 1988, in the name of Robert William Allington and assigned to the same assignee as this application, the disclosure of which is incorporated herein by reference.

In use, the capillary tube first is filled with an appropriate buffer solution or gel and then a small volume of sample introduced into one end of the capillary. Next the ends of the capillary tubing are inserted into two separate vessels each containing: (1) a predetermined volume of the same buffer solution that is in the capillary tube; and (2) a platinum electrode. The electrodes are connected to the power supply terminal cables, after which the power supply is turned on. The separated components or bands are detected by the detector.

In one type of prior art detector used in one class of capillary electrophoresis system, light is transmitted between the light source and the light sensor through the entire side of the capillary tube with light blocking members so as to utilize maximum light flux.

These two types of detectors each have a disadvantage. Without at least one single narrow aperture, some of the light flux passes through the medium to the detector, but other parts of the light flux bypass the medium. In such an embodiment, the flux passes around the medium through the walls of the quartz capillary tube and to the detector. This bypassed light results in a high level of background light which reduces the sensitivity of the detector.

A conventional method of reducing background light is to use one narrow slit and collimated light. This arrangement, if applied to capillary electrophoresis, has a disadvantage in that the light level at the detector is so low that there is excessive noise in relation to the strength of the electrical signals generated by the detector. This excessive noise is quantum noise.

One type of sample injector described in U.S. patent application 07/277,566 filed Nov. 29, 1988, injects very small samples by applying a vacuum on the end of the separating apparatus opposite to the source of the sample to draw a small portion of the sample into the separating apparatus.

This type of sample injector controls the amount of sample by timing the period through which the vacuum is applied. The time is determined by experience. This type of sample injector has a disadvantage of being bulky and expensive if it is to be precise.

Electromigratory sample introduction is also known. The general technique of electromigration sample injection for capillary electrophoresis is described by James W. Jorgensen in "New Directions in Electrophoretic Methods", ACS Symposium Series 335, American Chemical Society Washington, D.C., page 185 (September, 1985), the text of which is incorporated herein by reference. Electromigration or electrokinetic sample introduction involves placing both capillary tube inlet and high voltage electrode in the sample vessel and briefly turning on the power supply. A small amount of sample is drawn into the capillary by electrophoresis or electroosmotic flow which is caused by high voltage applied across the capillary ends. Then the power supply is turned off, the capillary and electrode are repositioned in the buffer reservoir, and the power supply is then turned on again to perform the separation.

Electromigratory sample introduction has several disadvantages, such as for example: (1) it introduces polar molecules at rates dependent on their charge and thus creates uncertainty; (2) some molecules may have a polarity that prevents their introduction; and (3) it can be expensive and difficult to use.

Split flow sample injectors are known in gas chromatographic systems and some liquid chromatographic systems. For example, the use of split injection is described in "Pressure and Composition Gradients in Capillary Supercritical Fluid Chromatography" by Clement R. Yonker and Richard S. Smith, *Anal. Chem.*, Mar. 1, 1989, 59, 727–731. Moreover, M. Gene et al. describes a sampler in "Electric Sample Splitter for Capillary Zone Electrophoresis", *J. Chromatography* 320, 159–165 (1985). This sampler works on the principle of secondary electrophoresis rather than split flow injection. It has the disadvantage of requiring a second power supply for the second electrophoresis direction.

The prior art systems, however, have several disadvantages such as: (1) they are used with sample injectors or high pressure flow apparatus and are not adapted for low velocity controlled manual injection such as that available by syringe injection; (2) it is difficult to isolate 30 kilovolts across the different "valve" positions normally used, which are the "load sample/inject" and "run" positions; and (3) there is substantial carryover from one run to the next. The need for complications such as a second power supply are undesirable features of some prior art systems.

SUMMARY OF THE INVENTION

Accordingly, it is an object of the invention to provide novel techniques for use in the separation sciences.

It is a further object of the invention to provide a novel sample injector.

It is a still further object of the invention to provide a novel control technique for sample injection in small quantities.

It is a still further object of the invention to provide for injection by electromigration as well as split flow injection.

It is a still further object of the invention to provide a novel manual capillary electrophoresis system.

In accordance with the above and further objects of the invention, a capillary electrophoresis apparatus includes a cabinet and an enclosure. The enclosure houses a sample injection system, a first buffer reservoir, a second buffer reservoir and an electrophoresis section. The cabinet supports the power supply and an absorbance detector with a sensing section extending into the cabinet and receiving the capillary in a flow cell for the sensing section. The sample injection and electrophoresis section include means for applying a potential across a capillary tube, split flow means for injecting samples into the capillary tube, means for removing samples from the tube and means for cleaning the tube.

The sensing section includes means for detecting samples electrophoresed through the tube.

Advantageously, the means for injecting a sample includes an injection block having an inlet means to receive a predetermined amount of sample and apply it to the capillary tube and means for bypassing the capillary tube with a predetermined amount of the sample, whereby errors from low volume injection are reduced. The injection block comprises a first inlet means adapted to tightly engage a portion of a syringe, a capillary tube inlet adapted to receive a portion of a capillary electrophoresis tube tightly enough to seal the port; and means for receiving surplus flow of sample. There is a common junction for the means for receiving surplus sample, means for receiving a portion of a capillary tube and the injection port means.

Some embodiments of electrophoresis apparatus further include means for purging the injection block means. This purging means includes means for closing the capillary input port and opening a flow port whereby purge liquid may be injected in the injection port to flow through said purge means and thereby remove traces of a prior sample. The apparatus may also advantageously include a purge block for filling or cleaning the electrophoresis tube, which block includes an inlet port for purge liquid and an electrophoresis tube port sized to receive a portion of the electrophoresis tube sufficiently snug to seal it, whereby fluid may be applied through said purge block and electrophoresis tube to purge said tube. The purge block may be used to deliver the electrophoresis medium into the tube.

Equipment constructed in accordance with the invention may be used for sample introduction by electromigration. For this purpose, a terminal post is provided on the injection block making electrical connection to the common junction of the injection block through an electrode introduced into the common junction of the injection block. For electromigration, the sample is first introduced into the junction, then the capillary tube is introduced and then an electric potential is established across the sample and the remote end of the capillary tube for a predetermined time.

From the above description, it can be understood that the separating apparatus of this invention has several advantages, such as for example: (1) it is suitable for use with very small-sensing-volume light-absorbance detectors, such as 1 to 10 nanoliters in sensing volume; (2) greater precision of sample injection is provided; (3) there is less sample carry-over from one run to another than some prior art injectors; (4) there is isolation of the injector from electrical high voltage which does not exist in the prior art; (5) the sample injection technique provides the benefits of split flow in a simple manual system; and (6) it is relatively simple to use.

SUMMARY OF THE DRAWINGS

The above noted and other features of the invention will be better understood from the following detailed description when considered with reference to the accompanying drawings, in which.

DETAILED DESCRIPTION

Figure 1:
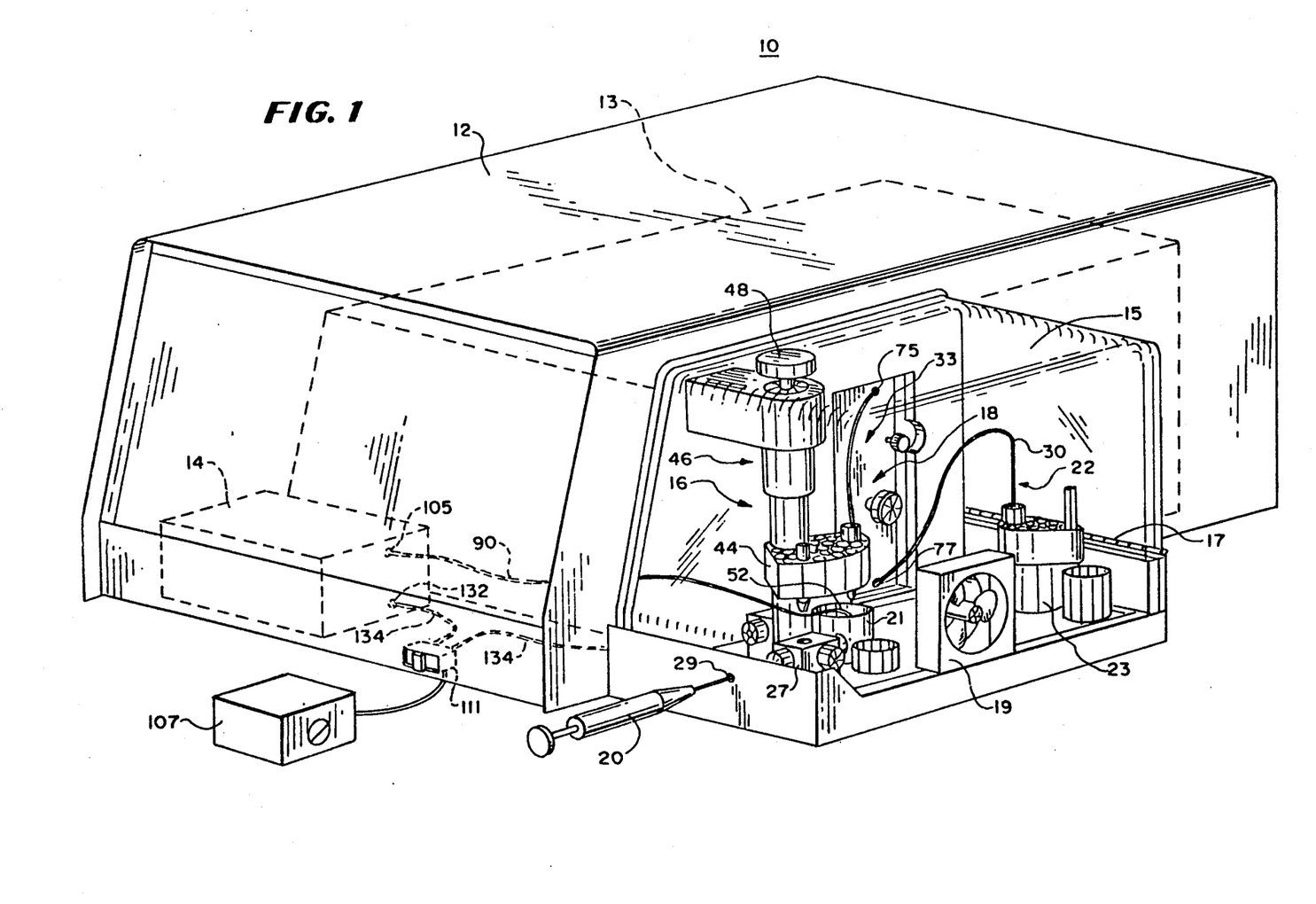
FIG. 1 is a simplified perspective view of an electrophoresis apparatus according to the invention including a sample injecting mechanism.

In FIG. 1, there is shown a capillary electrophoresis apparatus 10 having a cabinet 12, and an enclosure 15. The enclosure 15 houses a sample injection system 16, a sensing or detector section 18, a fan 19, a first buffer reservoir 21, a second buffer reservoir 23 and an electrophoresis section 22. The cabinet 12 supports the power supply 14 and an absorbance detector 13 forming part of the sensing section 18.

The electrophoresis section 22, the flow cell for the sensing section 18 and the sample injection system 16 are: (1) connected together and to the power supply 14 and absorbance detector 13 so as to separate molecular species; and (2) housed within an enclosure 15. The enclosure 15 may be formed of transparent Plexiglas (trademark of Rohm & Haas Co., Independence Mall West, Philadelphia, Pa., USA, for thermoplastic poly (methyl methacrylate)-type polymers)) that covers the flow cell access area for holding the buffer reservoirs 21 and 23, electrodes, capillary tubing, and sample injection mechanism. The high voltage lead of the power supply 14 is routed into the enclosure 15 which then is connected to the platinum electrodes (not shown in FIG. 1), located in first buffer reservoir 21 and the ground lead is connected to the platinum electrode (not shown) located in second buffer reservoir 23.

The enclosure 15 is constructed of thick transparent abrasion-resistant Plexiglas for high voltage insulation. The top and upper two-thirds of the front, left and right side form an access door which is hinged about a horizontal hinge 17 along the rear of the plastic enclosure 15. When opened, the access door pivots up and to the rear coming to rest in the space behind the enclosure 15. Opening the door operates a conventional electromechanical interlock to prevent serious electrical shock hazard. Also, the enclosure 15 is partially encased in grounded metal to protect the user from possible electrical creepage through the Plexiglas joint.

The sample injection section 16 includes the first buffer reservoir 21, a split flow injection block 27, a mechanism to move the capillary between the inject and run positions, and a mechanism to flush the capillary tubing with fresh new buffer or cleaning solution between runs. The enclosure 15 includes a grounded metal wall portion having a small injection port 29 through it aligned with an injection aperture in the split flow injection block 27 through which a sample can be supplied such as by a syringe 20.

The electrophoresis section 22 includes a capillary tube inlet carrier 44 for the inlet end of the capillary tube 30. The sensing section 18 is connected to the electrophoresis section 22 through a flow cell 33 that receives the capillary tube 30 and includes a light absorbance detection cell for monitoring the separation. The sensing volume of the flow cell 33 is between 1 and 10 nanoliters in the preferred embodiment. The capillary tube 30 enters and exits the flow cell 33 of the sensing section 18 at 75 and 77.

With this arrangement, the sample injection section 16 first is used to inject a sample into one end of the capillary tube 30 and then the capillary tube inlet carrier 44 puts that end into contact with the first buffer reservoir 21. The electrophoresis section 22 causes the other end of the capillary tube 30 to be in contact with a buffer in the second buffer section 23 and an electrical potential suitable for electrophoresis is applied across the buffer reservoirs.

More specifically, the sample injection system 16 injects sample into one end of the capillary tube 30 under pressure and flow rate conditions that minimize mixing with buffer and provides a precise, small volume of sample. Typical injection volumes are 1 to 30 nanoliters but a wider range is possible.

If the volume of the injected sample is too small, it may be difficult to detect bands without special techniques but it is probably possible to inject volumes as low as a quarter of a nanoliter. If the volume of the injected sample is too large, it may result in excessive band spreading but it is probably possible to obtain satisfactory results with some lengths of tube and internal diameters when the volumes injected for capillary electrophoresis are as large as 50 nanoliters.

After sample injection, an electrical potential is applied while the sample is within the capillary tube 30 to electrophores the sample. The bands separated by electrophoresis are sensed by transmitting light through narrow slits on opposite sides of the separating medium in the sensing section 18 and determining the light absorbance of the bands. In some embodiments, a single slit on one side of the separating medium may be used rather than two slits. The light typically is the ultraviolet region between 190 and 360 nanometers in wavelengths.

The capillary tube 30 is made of quartz in the preferred embodiment with an inside diameter of between 0.03 and 0.2 millimeter and may include any mobile separating medium. The capillary tube wall in the preferred embodiment is in the thickness range of between 0.1 and 0.2 millimeter. While a capillary tube of the conventional type for electrophoresis is contemplated for the preferred embodiment, other sizes of tubes and tubes of other materials may obviously be used.

The high voltage power supply 14 is located inside the cabinet 12 and is fitted with ground terminal 105 and high voltage terminal 132. The power supply 14 is preferably capable of supplying a regulated voltage from 1,000 to 40,000 volts at a current of up to 400 microamperes. A high voltage insulated cable or conductor 134 is connected to high voltage terminal 132 and terminates in platinum wire electrode 52. The ground terminal 105 is connected through lead 90 to the grounded metal case of the apparatus. The platinum electrode in second buffer reservoir 23 is also connected to the gounded metal case. Conductor 134 is in circuit with a switch 111 in the cabinet through a connector plug (shown for convenience on the side panel of FIG. 1 but actually on the back panel in the preferred embodiment) and can be shorted for normal operation or can connect conductor 134 in circuit with a conventional timer 107 to time electromigration sample introduction.

Figure 2:
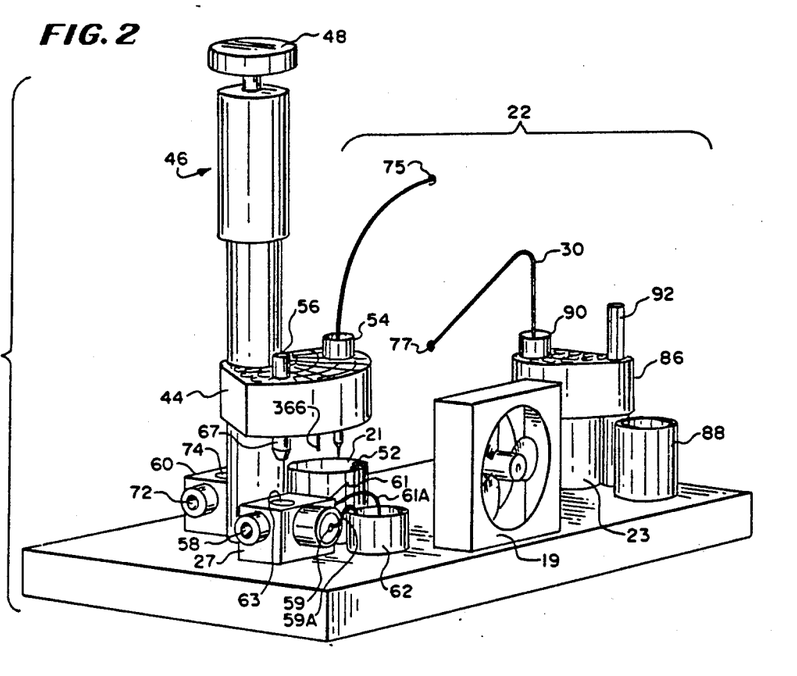
FIG. 2 is an enlarged perspective view of a portion of the electrophoresis apparatus of FIG. 1 in accordance with the invention.

In FIG. 2, there is shown a simplified perspective view of the sample injection system 16, the fan 19 and the electrophoresis section 22 mounted together for electrophoresis to illustrate the manner in which it may be set up and operated. To inject a sample, the access door to the electrophoresis section is first manually closed to prepare for sample injection and for applying a potential for electrophoresis with the lid closed and then the sample injection system is manually manipulated to inject a sample. Electrophoresis takes place in the closed compartment while the fan 19 provides circulating air for the removal of heat from the surface of the capillary tube 30. With the lid still closed, the sample injecting mechanism may be manually manipulated to provide for flushing of the sample injection block 27.

To manipulate one end of the capillary tube 30 for the purpose of sample injection and washing, the sample injection system 16 includes a capillary tube inlet manipulator 46, the sample injection block 27, a purge block 60, the first buffer block or reservoir 21, and a waste container 62. The capillary tube inlet manipulator 46 includes a handle 48 mounted to its top for movement therewith and a capillary tube inlet carrier 44. In the preferred embodiment, the capillary tube inlet manipulator 46 is manually operated by the handle 48 to move the capillary tube inlet carrier 44 from a position in which a sample may be injected into the capillary tube 30 through the sample injection block 27 to a position in which one end of the capillary tube 30 is within the first buffer reservoir 21 for electrophoresis. The capillary tube inlet manipulator 46 also can be moved to a position in which the inlet end of the capillary tube 30 is within the purge block 60 for flushing the capillary tube 30.

To permit injection of a sample by split flow into the capillary tube 30, the sample injection block 27 includes a syringe inlet port 58, a wash port 59, a splitter port 61 and a capillary tube cavity 63. With this arrangement, the capillary tube 52 may be inserted into capillary tube cavity 63 while the syringe 20 is inserted through the wall aperture or injection port 29 into the plastic enclosure 15 (FIG. 1) and into the aligned syringe inlet port 58 to supply a controlled amount of sample to the sample injection block 27. A portion of the sample flows from the splitter port 61 and a portion into the capillary tube 30.

To precisely control the volume cf sample injected into the capillary tube 30, a shorter length of larger inside diameter splitter capillary tube 61A is connected to the splitter port and leads to a waste disposal location. The fluid resistance of the splitter capillary tube 61A is much less than that of capillary tube 30, so most of the injected liquid discharges from the splitter capillary tube 61A. The ratio of the flows in capillary tubes 30 and 61A is precise and repeatable and allows the injection of microliter volumes into syringe inlet port 58 to load nanoliter volumes of sample into the capillary tube 30. This permits visual control of the total amount of sample injected into the sample injection block 27 by someone using a simple device such as a syringe and yet provides sample injection into the capillary tube 30 so small that it could not otherwise be conveniently controlled with a syringe alone. The wash port may be used when the sample injection block 27 is being flushed to prepare for a second sample injecting cycle.

To move the capillary tube 30, it is mounted through the capillary tube inlet holder 54 to be carried by the capillary tube inlet carrier 44. The capillary tube inlet carrier 44 is moved with the capillary tube inlet manipulator 46 to which it is mounted by turning the handle 48.

The user may hold the handle 48 and rotate the capillary tube inlet manipulator 46 about its vertical longitudinal axis to move the capillary tube inlet carrier 44 into position where the capillary tube 30 within the capillary tube inlet holder 54 can be inserted into the capillary tube cavity 63. In this position, the capillary tube inlet holder 54 forms a liquid tight seal around the capillary tube 30 which extends downwardly from its end and seals the upper portion of the capillary tube cavity 63 to permit the flow of sample into the capillary tube 30.

To permit flushing of the injection block 27, the capillary tube inlet carrier 44 includes a sealing peg 67 sized to seal the capillary tube cavity 63. When the capillary tube inlet holder 54 has been moved by the capillary tube inlet manipulator 46 to be within the buffer for electrophoresis, the sealing peg 67 is spaced a sufficient distance from it so that when it is lowered it seals the capillary tube cavity 63. Similarly, the first buffer reservoir 21 and the sample injection block 27 are positioned so that when the capillary tube inlet carrier 44 lowers the capillary tube 30 into the buffer for electrical connection, the sealing peg 67 seals the capillary tube cavity 63.

The waste container or reservoir 62 is positioned within the enclosure 15 (FIG. 1) adjacent to the wash port 59 so they may be conveniently connected and permit flushing of the sample injection block 27. Because the syringe inlet port 58 can receive a syringe when the high voltage is turned off, a wash solution may be applied while the sealing peg 67 seals the capillary tube cavity 63 to cause the fluid to flow into the waste reservoir 62 through the wash port 59 which communicates by a conduit 59A with the waste reservoir at this time. The splitter port 61 communicates through splitter capillary tube 61A with the waste reservoir 62.

To permit flushing of the capillary tube 30, the flush or purge block 60 includes a syringe port 72 and a capillary tube cavity 74 sized to receive the capillary tube inlet holder 54. With this arrangement, while the enclosure 15 (FIG. 1) is open, the capillary tube 30 may be moved by lifting and turning the capillary tube inlet manipulator 46 until the capillary tube inlet holder 54 is over the port or capillary tube cavity 74, lowering the end of the capillary tube 30 into the cavity to close the common junction of the flush block 60 with the end of the capillary tube 30 and with the capillary tube inlet holder 54 in the capillary tube cavity 74. A syringe is inserted in the syringe port 72 with the end of the capillary tube 30 in the flush block 60 to apply a flushing liquid through the flush block 60 and through the capillary tube 30 into a waste container to be described hereinafter.

To permit electrophoresis, the electrophoresis section includes the capillary tube 30, the outlet moving mechanism 86, a second waste container 88, the platinum electrode buffer container 23, a second capillary holder 90, and a handle 92. The outlet moving mechanism 86 is positioned over the platinum electrode buffer container 23 and adapted to be rotated about its axis by the handle 92 so that the second capillary tube holder 90 may be positioned over the platinum electrode buffer container 23 for electrolysis and moved to a position over the second waste container 88 during a flushing operation.

With this arrangement, one end of the capillary tube 30 is inserted in the first buffer reservoir 21, the other end of the capillary tube 30 may be rotated over the second buffer reservoir 23 and lowered by the handle 92 for electrolysis. During a flushing operation, the capillary tube 30 may be rotated by the capillary tube inlet manipulator 46 to be inserted sealingly in the capillary tube cavity 74 of the flush block 60 while the other end of the capillary tube 30 is moved and the second capillary holder 90 over the second waste container 88 so that a syringe may apply a flushing liquid through the syringe port 72, the capillary tube 30 and into the second waste container 88.

Figure 3:
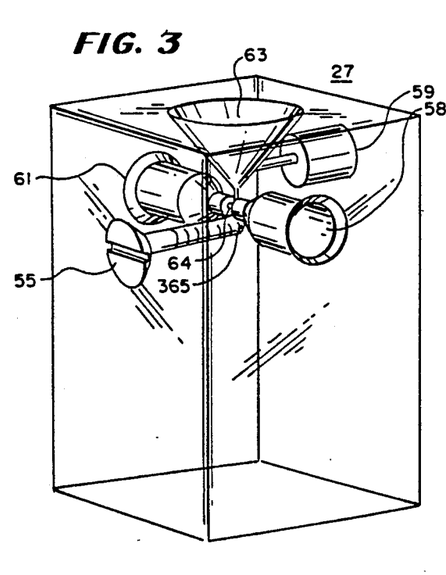
FIG. 3 is a perspective view of a portion of the apparatus of FIG. 2.

In FIG. 3, there is shown an enlarged perspective view of the sample injection block 27 having six walls forming a hollow right regular parallelopiped with the syringe port 58, splitter port 61 and an end of the capillary tube cavity 63 meeting at a junction 64. This junction 64 is a meeting of three cylindrical tubes having diameters only larger than the inner diameter of the capillary tube 30 (FIGS. 1 and 2) by an amount so that the capillary tube 30 may be moved into communication with the syringe port 58 and the splitter port 61 tightly enough to seal the ports.

To receive the syringe 20, the syringe port 58 is formed of a plastic having an internal diameter slightly larger than the diameter of the needle of a syringe but terminating in an end having an internal diameter forming a sealing relationship with the tip of the needle of the syringe. Similarly, the splitter port 61 is enlarged so that at its output end, it may communicate through a splitter tube with a reservoir for receiving surplus sample. The wash port 59 communicates with the capillary tube cavity 63 at a level above the junction 64 to receive fluid when the sample injection block 27 is being flushed by insertion of a syringe in the syringe port 58 with the splitter port 61 closed and injecting a flush liquid.

The capillary tube cavity 63 is generally funnel-shaped and terminates in a tubular passage of diameter slightly larger than the outside diameter of the capillary tube 30. This tubular passage terminates at junction 64 to bring the end of the capillary tube 30 to the location of the junction. This enables the capillary tube 30 to receive a precise proportion of the fluid injected by a syringe into the syringe port 58. The upper end of the funnel of the capillary tube cavity 63 is sized to fit the lower end of capillary tube inlet holder 54 (FIG. 2), for convenient alignment with the capillary tube 30.

In one embodiment, a terminal post 55 (FIG. 2) which is a stainless steel screw is mounted to the walls of the sample injection block 27 for easy electrical connection of its point to the power supply 14 (FIG. 1). The terminal post 55 is electrically connected to the junction 64 where a platinum electrode permits electrical connection of this junction 64 to the terminal 132 of the power supply 14. This embodiment enables sample introduction by electromigration to be performed using the injection block 27 since power can be applied across the sample and the capillary tube 30, the exit end of which is electrically grounded through a buffer.

To provide for such electromigratory sample introduction, a stainless steel screw 55 with a small platinum tip 365 (FIG. 2) screws into the body of sample injection block 27. The screw 55 forms a tight seal and the platinum tip 365 protrudes into junction 64. The capillary tube inlet carrier 44 (FIG. 2) includes a connecting flexible bar 366, which is permanently connected to the high voltage lead 134 (FIG. 1) of the power supply 14. When the capillary tube 30 is in buffer compartment 21 (FIG. 2), the connecting flexible metal bar 366 has no contact with any part of the system. When the capillary tube 30 is in the sample introduction position inside injection block 27, the connecting flexible bar 366 makes electrical contact with the stainless steel screw 55 with platinum tip 365.

Figure 4:
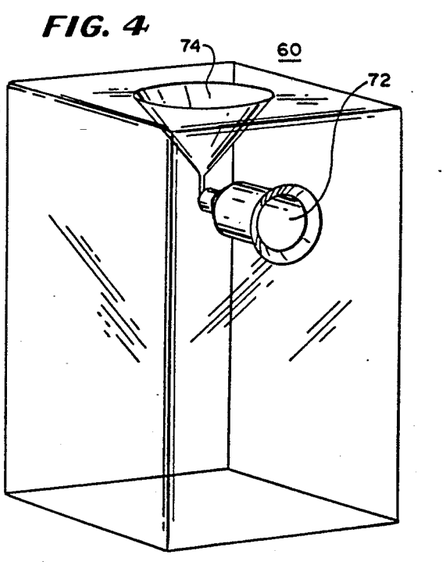
FIG. 4 is a perspective view of still another portion of the electrophoresis apparatus of FIG. 2.

In FIG. 4, there is shown a flush block 60 shaped as a right regular parallopiped having walls on all sides and a hollow interior. In one side, the syringe port 72 opens and in the other side, there is a funnel-shaped capillary tube cavity 74 with the syringe port 72 and capillary tube cavity 74 being designed for substantially the same purposes as the syringe port 58 and capillary tube cavity 63 of the injection block 27 (FIG. 3). However, the junction 79 need only be a junction between the syringe port 72 and the bottom of the capillary tube cavity 74 so that the syringe needle forms a seal with the end of the syringe port 72 and the capillary tube 30 and its capillary tube holder 54 forms a sealing relationship with the inner portion of the capillary tube cavity 74, permitting fluid to be injected by the syringe 20 (FIG. 1) directly into the capillary tube 30 (FIGS. 1 and 2) to flush the capillary tube 30.

One end of the capillary tube 30 is firmly held to the inlet moving mechanism using a specially designed ferrule assembly. The other end of the capillary enters a flow cell in the detector section 18 (FIG. 1) through one of the holes on the cassette holder and exits from the second hole on the cassette. The flow cell has a detection volume within which separated electrophoresed bands are sensed. To allow sensing small enough bands, this detection volume should be less than 100 nanoliters.

The flow cell may be equipped with fixed or adjustable slits to align a very narrow measuring light beam so that it goes exactly through the liquid filled part of the capillary tube 30. The capillary tube 30 then goes through the second ferrule assembly and is held firmly to the outlet moving mechanism opposite the other end of the capillary tube 30. An example of a suitable flow cell and its component parts is described herein having adjustable slits. However, any suitably designed flow cell may be used including one with fixed apertures. The description is intended merely as an example of a flow cell usable for capillary electrophoresis.

To inject sample into the capillary tube 30, the capillary tube 30 is positioned inside the capillary tube cavity 63 of the injection block 27 (FIG. 3). A 10 ul or smaller syringe 20 (with a 22 gauge, blunt end stainless steel needle) is filled with sample solution and the needle is then inserted in injection port 29 (FIG. 1). A known volume of sample is then injected. According to the principle of split flow injection, most of the sample goes through the short, larger diameter splitter capillary tube 61A connected to splitter port 61 and a very small volume of the sample is introduced into the long, smaller diameter capillary tube 30.

The amount of sample can be controlled with precision and reproducability because: (1) the division between the flow into the capillary tube 30 and splitter capillary tube 61A is precise and known from their dimensions; and (2) the amount dispensed from the syringe 20 (FIG. 1) can be controlled to a low and reasonable percentage. This low percentage is close to the percentage error in the sample injected into the capillary tube 30 because the ratio of total sample from the syringe 20 injected into the injection block 63 (FIG. 3) to the portion of the sample placed in the capillary tube 30 is quite repeatable.

In one embodiment, the capillary tube 30 has a 50 um (micrometer) inside diameter and is 80 cm (centimeter) long and the splitter capillary tube 61A has 125 um inside diameter and is 3 cm long. A 5 to 10 ul (microliter) injection loads about 5 to 10 nl into the capillary tube 30.

After sample is injected, the capillary tube 30 is moved to the run position. This is done by raising a handle on top of the enclosure and rotating it 90 degrees counter-clockwise. The handle is then lowered to place the capillary tube 30 in the running buffer.

When the capillary tube 30 is in the buffer reservoir 21, the syringe 20 is removed from syringe port 58 and the high voltage power is turned on to start the separation. There are safety interlocks located on the syringe inlet port 58 and on the manual capillary manipulator. These prevent voltage from being applied when the capillary tube 30 is not in the run position or if a syringe 20 is in the injection port. Also, a fan 19 is incorporated inside the enclosure 15 to circulate the air inside the compartment. This facilitates heat dissipation from the surface of the capillary tube 30 during a run and hence minimizes the absorbance noise and drift.

When the capillary is in the first buffer reservoir 21, capillary tube cavity 63 in the sample injection block 27 (FIG. 3) is automatically plugged by the sealing peg 67 (FIG. 2) attached to the manual capillary manipulator. This allows the injection block 27 to be flushed with buffer before the next sample. The wash solution is introduced through syringe inlet port 58 using a syringe similar to that used for sample introduciton except having larger volume. Most of the wash fluid flows through wash port 59 and conduit 59A to the waste container 62.

To flush the capillary tube 30 with fresh buffer or cleaning solution, the access door on the enclosure 15 is opened to gain access to the flush mechanism. The capillary tube 30 is positioned inside the capillary tube cavity 74 of the flush block 60 using the handle 48 on top of the compartment and the outlet of the capillary tube 30 is placed inside the second waste container 88 by rotating the outlet moving mechanism 86 through 90 degrees counterclockwise. A similar syringe as described earlier is filled with buffer or cleaning solution and injected into the capillary tube 30 using syringe port 72 on the flush block 60. The syringe is then removed, the outlet of the capillary tube 30 is placed inside the second buffer reservoir 23, the access compartment door is closed, and the inlet of the capillary tube 30 is positioned into the first buffer reservoir 21 or capillary tube cavity 63 to continue the operation.

The sensing section 18 (FIG. 1) includes an absorbance monitor 13 and a sensing section 18. The absorbance monitor 13 and sensing section 18 utilize the optics, circuitry and structure of the absorbance detector described in U.S. Pat. Nos. 4,726,680 and 4,523,097 for liquid chromatography absorbance detectors. The absorbance monitor 13 incorporates a light source for illuminating one side of the sensing section 18 and a light detector for detecting light exiting the opposite side of sensor. Of course, the flow cell and separating system are adapted for capillary electrophoresis as described herein, instead of for liquid chromatography as described in the foregoing patents.

Figure 5:
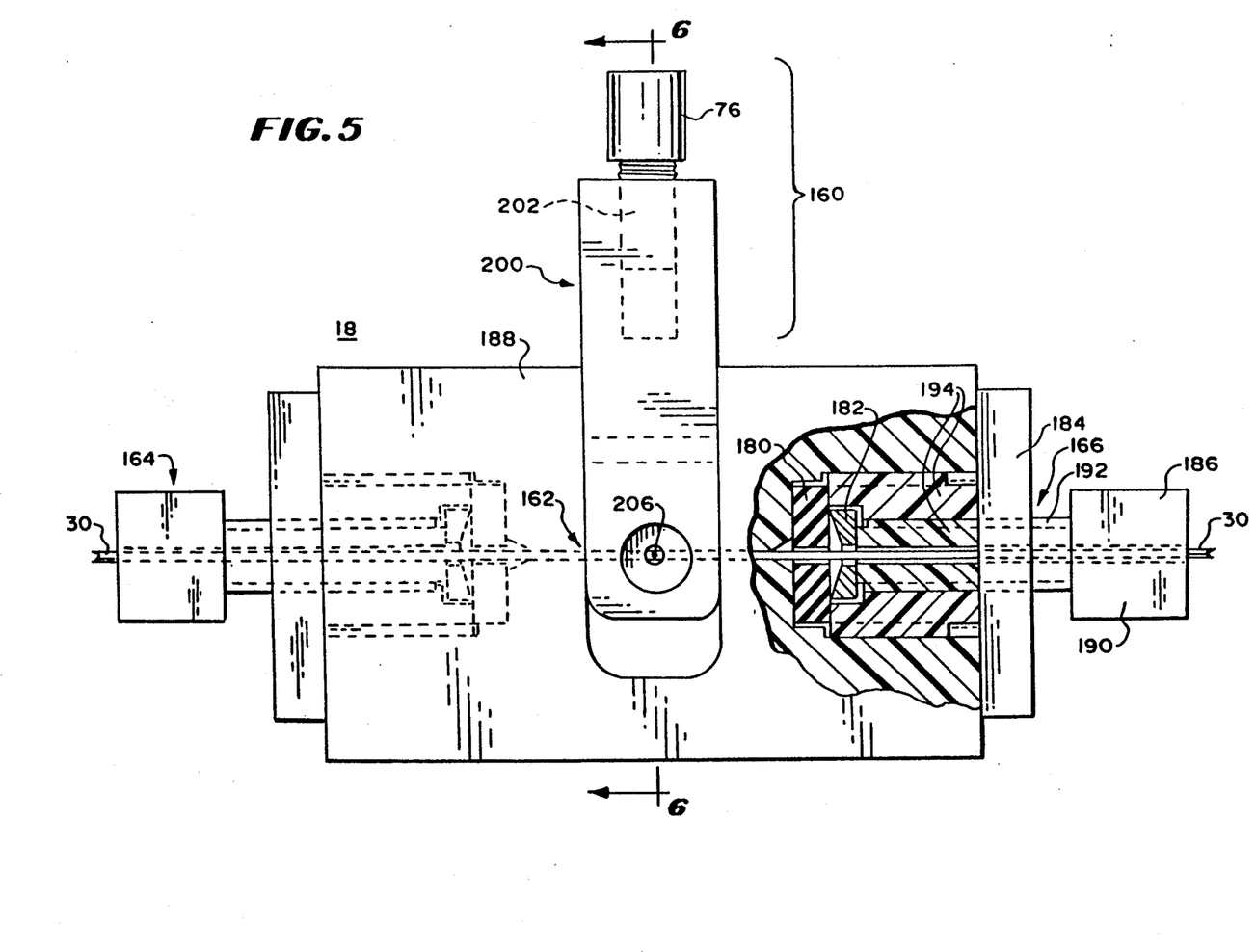
FIG. 5 is a broken away, partly-sectioned view of still another portion of the apparatus of FIG. 1.

In FIG. 5, there is shown a side view partly broken out and sectioned showing one embodiment of sensing section 18, disclosed in U.S. application Ser. No. 07/277,566 filed Nov. 29, 1988, in the name of Robert William Allington and assigned to the same assignee as this application (the disclosure of which is incorporated herein). The sensing system 18 has an adjustment section 160, an optical slit section 162, a first fitting assembly 164 for the capillary tube 30, and a second fitting assembly 166 for the capillary tube 30. The capillary tube 30 is received in the first and second fitting assemblies 164 and 166, which cause the capillary tube 30 to extend along the axis of the sensing section 18 and between the slits in the optical slit section 162. The location of the two slits in a direction perpendicular to the axis of the capillary tube 30 is adjusted by the adjustment section 160.

The sensing section 18 is attached to a cassette or mounting plate for mounting in the absorbance monitor 13 (FIG. 1) and receives the capillary tube 30. To mount the capillary tube 30, the two fitting assemblies 164 and 166 are adjustable. They are identical in structure and only the fitting assembly 166 will be described in detail herein.

The second fitting assembly 166 includes a rubber washer 180, a stainless steel squeezer 182, a plastic threaded closure 184 and a plastic threaded fastener 186. The threaded fastener 186 is positioned to be tightened to hold the threaded closure 184 in place where it supports a threaded sleeve. The threaded fastener 186 also presses the stainless steel squeezer 182 against the rubber washer 180 so as to provide a seal around the capillary tube 30.

In one embodiment, the housing 188 of the sensing section 18, the threaded fastener 186 and the threaded closure 184 are all formed of a relatively hard plastic such as Delrin (trademark of the DuPont Corporation). The washer 180 is a flexible, elastomeric material which may be the thermoplastic rubber Kraton (trademark). A central aperture extends through the washer 180, the stainless steel squeezer 182, the threaded closure 184 and the fastener 186 to accommodate the capillary tube 30 which extends along the longitudinal axis, past the optical slit section 162 where the optical sensing is performed and through the fitting assembly 164 on the opposite side of the sensing section 18.

The force the washer 180 around the capillary tube 30, the washer 180 is generally cylindrical with a cylindrical central opening receiving the capillary tube 30. It fits conformably in a counterbore within the housing 188 of the sensor. The stainless steel squeezer 182 is generally cylindrical but has an inwardly tapering cone positioned adjacent to the washer 180 and a central aperture to accommodate the capillary tube 30 so that when it is pressed inwardly, it forces the washer 180 inwardly towards its central opening and outwardly against the counterbore.

The force the stainless steel squeezer 182 against the washer 180, the threaded fastener 186 includes a thumb handle 190 and a threaded shank 192, with the threaded shank 192 extending downwardly through the plastic threaded closure 184 where it engages a correspondingly threaded metal sleeve 194 threaded into a tapped hole of the Delrin housing. The threads within the tapped hole are within a metal sleeve molded within the aperture of the Delrin housing so as to remain fixed in position and still accommodate threads. The mechanism of the fittings are designed to accommodate the capillary tube 30 in such a way that the capillary tube 30 is held immobile in the sensing section 18.

The adjustment section 160 includes an adjustment screw 76 fixedly mounted (by convential means not shown in the figure) with respect to the housing 188 and an optical slit carriage 200. The optical slit carriage 200 is stainless steel and threaded at 202 in its upper portion with internal threads complementary to the external threads on a shank of the adjustment screw 76 so that as the adjustment screw 76 is rotated, the carriage is moved up and down with respect to the housing 188 of the sensing section 18.

Figure 6:
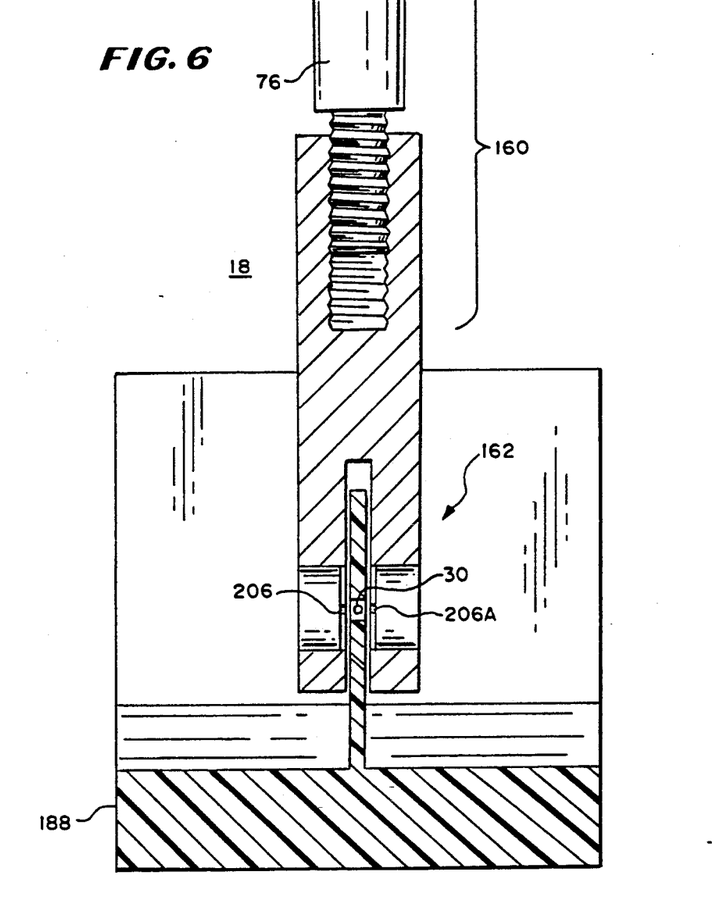
FIG. 6 is a partly-sectioned view of the apparatus of FIG. 5.

The optical slit section 162 is mounted to the bottom of the optical slit carriage 200 so as to be raised and lowered therewith and includes on each side a relatively short optical slit 206 having a longitudinal axis aligned with the longitudinal axis of the capillary tube 30. There are two such slits which closely straddle the capillary tube 30 (FIG. 5) a cross section through line 6—6 of FIG. 5, more clearly shown the relationship of the two slits 206 and 206A to the capillary tube 30. FIG. 6 shows the narrow dimension of the slits, which is 100 micrometers in the preferred embodiment. Preferably, the distance between the slits is between one and three times the outside diameter of the capillary tube 30.

More specifically, the rubber washer 180 is compressed around the capillary tube 30 to hold the tube in place. The rubber washer 180 preferably is made of white, food grade, Kraton (trademark) thermoplastic rubber which does not deposit any ultraviolet light absorbing materials on the quartz tube as the tube is pushed through the washer. Kraton is available from Shell Corporation. The rubber is compressed radially to tighten around the tube by pushing the female cone-shaped stainless steel squeezer 182 against it by turning a plastic threaded fastener 186. The threaded fastener 186, stainless steel squeezer 182 and washer 180 are captivated within the housing 188 of the light sensor by the threaded closure 184 which screws into a threaded recess in the housing 188. The tightener, captivator and housing are advantageously made out of Delrin (trademark of DuPont) plastic.

The optical slit carriage 200 is moved with the adjustment screw 76 to center a pair of optical slits, one of which is shown at 206, each being 0.01 inch (250 micrometers) long by 0.004 inch (100 micrometers) wide, over the capillary tube 30 extending through the light sensor. The dual slits are exactly corresponding elements mounted exactly opposite each other across a bifurcation of the optical slit carriage (FIG. 6). The capillary tube 30 lies within the bifurcation. The long direction of the slit is parallel to the axis of the capillary tube 30. When the adjustment screw 76 is turned, the optical slit 206 moves transversely with respect to the capillary tube 30. The capillary tube 30 is firmly held within the bifurcation by two holders.

To use the light sensor, first the protective polyimide protective coating of the quartz capillary tube 30 must be removed because it absorbs ultraviolet light. This is easily done by burning it off with a match or cigarette lighter in the region which is to be located between the optical slits. After burning the coating off, the capillary tube 30 must be cleaned with very pure acetone. Any area of the capillary tube 30 that does not have an intact polyimide coating is very fragile and must be handled with more than normal care.

Both Delrin tighteners on the sensing section 18 are loosened, and the capillary tube 30 is gently fed through one tightener, through the rubber washer, through the optical slit region, through the other washer and tightener, and moved to the desired position with the polyimide-free region of the capillary tube 30 between the slits. Then the two tighteners are screwed down finger tight, thus firmly captivating the capillary tube 30 in the light sensor.

The sensing section 18 is inserted in the absorbance monitor 13 located within the cabinet 12 in FIG. 1. In FIG. 1, the sensor is generally shown at 18. The capillary tube 30 is filled with water or buffer. Light from the light source of the absorbance monitor 13 enters one of the pair of slits 206 or 206A in the sensing section 18, and when the sensing section 18 is properly adjusted, light exits the other slit and impinges upon the light detector of the absorbance monitor 13. To make this adjustment, the adjustment screw (shown as 76 in FIGS. 5 and 6), is rotated and the indication of the absorbance monitor 13 is monitored. Starting at one extreme of rotation on the adjustment screw 76, and referring to FIG. 7, the following is observed.

Figure 7:
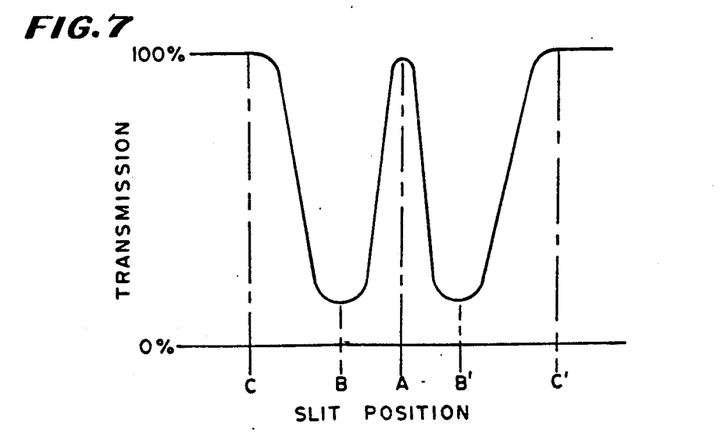
FIG. 7 is a graph illustrating the operation of the apparatus of FIGS. 5 and 6.

At slit position C, the slit is entirely beyond the capillary tube 30 and light travels through the free space between the pair of slits. As the adjustment screw 76 is rotated, the light beam cuts through the curved edge of the capillary tube 30 which deflects most of the light going through the first slit so it does not go through the second slit. At slit position B, almost all of the light is lost, and a minimum of light transmission is indicated on the absorbance monitor 13.

Assuming that the capillary tube 30 is properly filled with water or electrolyte buffer (no air in the tube at the light path), continued rotation of the adjustment screw 76 so that the pair of slits are centered on the tube greatly increases the transmission again, to a well defined maximum at proper alignment. This is shown as slit position A in FIG. 7.

Further rotation of the adjustment screw 76 produces transmission indications as shown when moving from A to B' and then from B' to C' because of symmetry in the transverse direction. The absorbance monitor 13 should be operated with the adjustment screw 76 set to slit position A, as determined from the local maximum transmission reading of the absorbance monitor 13 itself.

Figure 8:
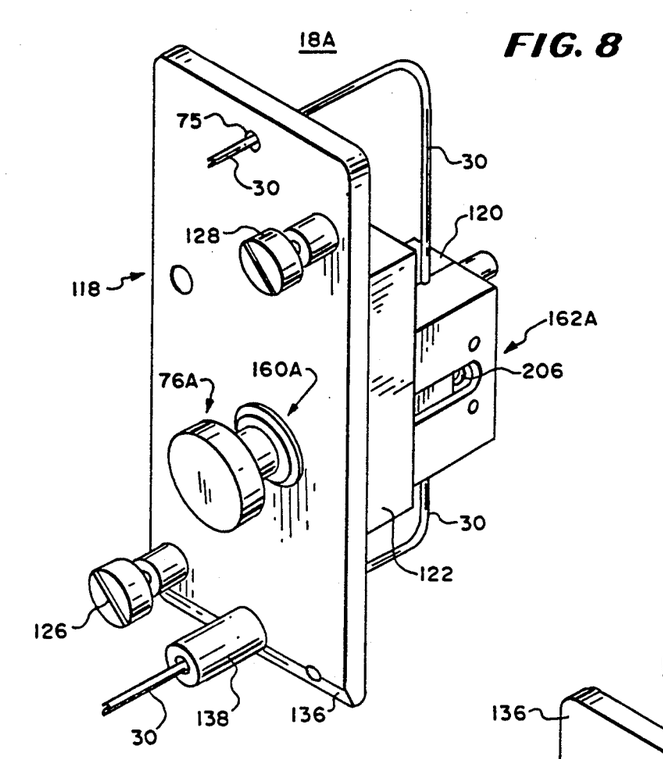
FIG. 8 is a perspective view of one side of a portion of the apparatus of another embodiment of flow cell forming a part of the apparatus of FIG. 1.

In FIG. 8, there is shown another embodiment of flow cell assembly 18A having a cassette or mounting plate 118, a stationary block 120, a spacer block 122, and an optical slit screw adjustment assembly. The stationary block 120, spacer block 122 and screw adjustment assembly are supported by the mounting plate 118 in the absorbance detector 13 (FIG.1).

The screw adjustment assembly is similar to the adjustment section 160 in the embodiment of FIG. 5 and controls an optical slit section 162A shown more completely in FIGS. 5 and 6. It is adjusted by the screw adjustment 76A in a manner described in connection with the adjustment screw 76 in the embodiment of FIGS. 5 and 6. As described in connection with the embodiments of FIGS. 5 and 6, an optical slit carriage is moved with the screw-adjustment to center a pair of optical slits, each of which is 0.01" (250 micrometers) long by 0.004" (100 micrometers) wide, over a capillary tube extending through the flow cell in a manner similar to the flow cell 18. The dual slits are exactly corresponding elements mounted exactly opposite each other across a bifurcation of the optical slit carriage. The capillary tube 30 lies within the bifurcation. The long direction of the slit is parallel to the axis of the capillary tube 30.

When the screw adjust is turned, the slit moves transversely with respect to the capillary tube 30. The capillary tube 30 is firmly held within the bifurcation by a spring-loaded holding mechanism. The flow cell body and holding mechanism are made of aluminum with anodized surface finishes.

The mounting plate 118 is mounted to the absorbance monitor 13 by mounting screws 126 and 128 and receives the capillary tube 30 to support a portion of it between the two electrodes applying potential for electrophoresis. The capillary tube 30 enters through an aperture 75 at the top and returns outwardly through a fixture 138 after passing through the optical slit for detection of bands through the aperture 206 in the stationary block 120. With this arrangement, the capillary tube 30 may be adjusted as described in connection with the embodiment of FIGS. 5 and 6 from inside the enclosure 15 (FIGS. 1 and 2).

Figure 9:
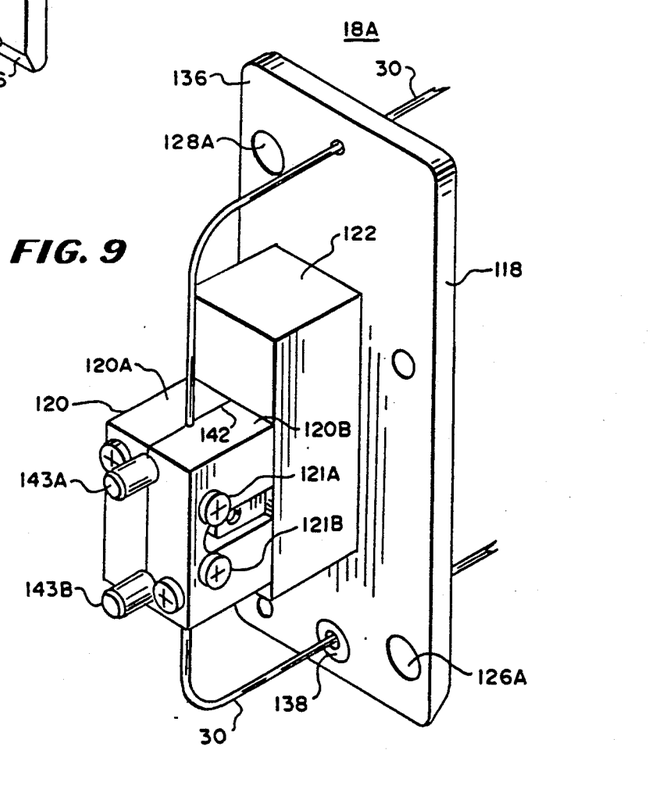
FIG. 9 is another perspective view of the apparatus of FIG. 8.

In FIG. 9, there is shown a perspective view of the flow cell from the absorbance monitor side showing the stationary block 120 and spacer 122. The stationary block 120 includes first and second sections 120A and 120B held together by screws 121A and 121B. Two guide rods 143A and 143B extend inwardly against an inward spring-loaded movable blade 142 which positions the capillary tube 30 to hold it in place. While a split block is shown, any other clamping device may be used to firmly position the capillary tube 30.

To insert the capillary tube 30, the capillary tube 30 is positioned between the stationary block 120 and spring-loaded movable blade 142. The spring-loaded movable blade 142 is pushed in by finger pressure on the two guide-rods 143A and 143B and the capillary tube 30 then is passed through the opening on top of stationary block 120, with the polyimide-free region of the tubing between the slits. The guide-rods 143A and 143B are released and the capillary tube 30 is sandwiched between the stationary block 120 and the spring-loaded moving blade 142. The ends of the capillary tube 30 then are passed through the holes on the flow cell cassette holder. The use of the stationary block 120 and adjustable blade 142 to hold the capillary tube 30 in place is not part of this invention.

To introduce a sample into the capillary tube 30 by electromigration, junction 64 (FIG. 3) is filled with the sample by means of syringe 20 through syringe inlet port 58. Syringe 20 is removed and the capillary tube 30 is positioned inside the capillary tube cavity 63 as described earlier. Next, the electromigration introduction time is set on a conventional timer 107 (FIG. 1), which is connected to provide activation of the high voltage power supply for a controlled time duration; such as several seconds. The power supply typically is set to a few thousand volts for sample introduction. The timer is then activated to turn on the power supply and effect the introduction. After the time is expired, capillary tube 30 is moved into the first buffer compartment 21 by capillary tube inlet carrier 44, and the high voltage is reactivated at a voltage typically higher than that used for sample introduction. This higher voltage effects the separation as described previously.

The repeatability of the sample volume introduced by the split-flow technique as described here is better than a more conventional vacuum sample introduction method. The following Table 1 is comparison data which indicates the repeatability of split-flow sample introduction using three runs with the split-flow injection method. The sample was a standard mixture of 300 ug/ml dansylated isoleucine, serine and methionine as compared to injection using a vacuum pump under identical experimental conditions. The volume of sample introduced into the capillary tube can be manipulated either by adjusting the volume of the sample in the syringe or varying the length or internal diameter of the splitter tube or both. Injection by electromigration also provides satisfactory repeatability for most purposes.

The separated sample zones migrate through the sensing section 18 and are recorded by the absorbance monitor 13. When the separation is complete, the enclosure 15 is opened, capillary inlet tube manipulator 46 is moved to move the end of the capillary tube 30 from the first buffer reservoir 21 into the injection block 27, a new sample is injected, the capillary tube inlet manipulator 46 is moved to place the end of the

TABLE 1

| Peaks | Migration time (sec) | Peak Height | Peak Area |
|---|---|---|---|
| SPLIT FLOW INJECTION | | | |
| 1 | 366.7 ± 0.3% | 2183.3 ± 0.5% | 8445.7 ± 1.5% |
| 2 | 476.5 ± 0.3% | 1584.7 ± 2.6% | 8056.3 ± 1.2% |
| 3 | 599.0 ± 0.3% | 1686.3 ± 2.5% | 9998.3 ± 1.4% |
| VACUUM INJECTION | | | |
| 1 | 376.7 ± 1.7% | 2311.7 ± 0.1% | 10523.0 ± 2.3% |
| 2 | 491.5 ± 2.0% | 1836.7 ± 1.0% | 10442.0 ± 2.3% |
| 3 | 576.9 ± 2.1% | 1993.7 ± 1.3% | 13031.0 ± 2.6% | capillary tube 30 in the first buffer in reservoir 21 and the operation cycle repeats for the next sample.

From the above description, it can be understood that the separating apparatus of this invention has several advantages, such as for example: (1) it is suitable for use with very small sensing volume light absorbance detectors, such as 1 to 10 nanoliters in sensing volume; (2) greater precision of sample injection is provided; (3) there is less sample carry-over from one run to another than some prior art injectors; (4) there is isolation of the injector from electrical high voltage which does not exist in the prior art; (5) the sample injection technique provides the benefits of split flow in a simple manual system; and (6) it is relatively simple to use.

Although a preferred embodiment of the invention has been described with some particularity, many modifications and variations are possible in the preferred embodiment in the light of the above teachings. Therefore, it is to be understood that, within the scope of the appended claims, the invention may be practiced other than as specifically described.

What is claimed is:

1. Apparatus for detecting bands in a capillary tube having a predetermined direction of motion in a separation medium within the capillary tube comprising:
    a cabinet;
    an enclosure mounted to the cabinet;
    said enclosure being openable to permit manual opertion of the apparatus;
    a capillary tube adapted to contain a separating medium;
    power supply means for applying an electrical potential across said capillary tube;
    said power supply means including a power supply within said cabinet;
    flow cell means located within a detector means including a detector and a detection volume;
    said detection volume being less than 100 nanoliters;
    said flow cell means including means for holding the capillary tube within the detector means;
    said capillary tube having a diameter no greater than 700 micrometers;
    split-flow means for injecting samples into said tube;
    said split-flow means being within said enclosure and at least a portion of said flow cell means being within said cabinet;
    means for permitting said capillary tube to pass from said enclosure through said flow cell and;
    opening means having internal walls defining an opening into said enclosure for enabling sample to be injected into said split flow means without opening said enclosure, whereby the interior of the enclosure is not exposed during sample injection.

2. Apparatus according to claim 1 in which the opening means is adapted to cooperate with a syringe for injecting sample.

3. Apparatus according to claim 1 in which the enclosure includes switch means for inactivating the power supply upon opening the enclosure.

4. Apparatus for detecting bands in a capillary tube having a predetermined direction of motion in a separation medium within the capillary tube comprising:
    a capillary tube adapted to contain a separating medium;
    means for applying an electrophoresis separation electrical potential across said capillary tube;
    a detector means incorporating a detection volume not larger than 100 nanoliters;
    said detector means including means for removably holding the capillary tube within the detector;
    said capillary tube having a diameter no greater than 700 micrometers;
    split-flow means for injecting samples into said tube;
    said split flow means incorporating high voltage isolating means;
    injection block means;
    said injection block means having a first inlet means to receive a predetermined amount of sample;
    said injection block means further including means for dividing the sample applied to the inlet in a precise ratio with one conduit means receiving a predetermined proportion of sample not supplied to said capillary tube and a capillary tube recepticle for applying a predetermined amount of sample to said capillary tube; and
    electromigration sample introduction means in said injection block.

5. Apparatus for detecting bands in a capillary tube having a predetermined direction of motion in a separation medium within the capillary tube comprising:
    a capillary tube adapted to contain a separating medium;
    means for applying an electrophoresis separation electrical potential across said capillary tube;
    a detector means incorporating a detection volume not larger than 100 nanoliters;
    said detector means including means for removably holding the capillary tube within the detector;
    said capillary tube having a diameter no greater than 700 micrometers;
    split-flow means for injecting sample into said tube;
    said split flow means incorporating high voltage isolating means;
    said split flow means further including a common junction between said first inlet means, conduit means and capillary recepticle;
    said capillary recepticle including inlet means for receiving a portion of a capillary tube;
    said inlet means for receiving a portion of a capillary tube communicating with said common junction means, whereby a portion of the sample applied to said common junction means enters said capillary tube means and another portion is transmitted through said conduit means; and injection block purge means, said injection block purge means including a second purge conduit means and means for closing said capillary tube inlet means whereby purge fluid may flow into said purge conduit means while said conduit means and electrophoresis tube means are sealed.

6. Apparatus according to claim 5 further including:
a capillary tube purge means;
said capillary tube purge means including purge block means having a first opening sized to sealingly receive a portion of a capillary tube and second inlet means adapted to receive a means for injecting a purge liquid;
said second inlet means and first opening being joined and containing continuous walls with no outlet openings to the flow of fluid whereby fluid injected in said purge means is applied directly to said capillary column means to purge said column.

7. Apparatus according to claim 6 in which said electrophoresis tube purge means includes mean for supplying electrophoretic medium to said capillary tube.

8. Apparatus for detecting bands in a capillary tube having a predetermined direction of motion in a separation medium within the capillary tube comprising:
a capillary tube adapted to contain a separating medium;
means for applying an electrophoresis separation electrical potential across said capillary tube;
detector means incorporating a detection volume not larger than 100 nanoliters;
said detector means including means for removably holding the capillary tube within the detector;
said capillary tube having a diameter no greater than 700 micrometers;
split-flow means for injecting samples into said tube;
said split flow means incorporating high voltage isolating means and injection block means;
said injection block means having a first inlet means to receive a predetermined amount of sample;
said injection block means further including a means for dividing the sample applied to the inlet in a precise ratio with one conduit means receiving a predetermined proportion of sample not supplied to said capillary tube and a capillary tube recepticle for applying a predetermined amount of sample to said capillary tube;
said split flow means further including a common junction between said first inlet means, conduit means and capillary recepticle;
said capillary recepticle including inlet means for receiving a portion of a capillary tube;
said inlet means for receiving a portion of a capillary tube communicating with said common junction means, whereby a portion of the sample applied to said common junction means enters said capillary tube means and another portion is transmitted through said conduit means; and
injection block purge means, said injection block purge means including a second purge conduit means and means for closing said capillary tube inlet means whereby purge fluid may flow into said purge conduit means while said conduit means and electrophoresis tube means are sealed.

9. Apparatus according to claim 8 further including:
a capillary tube purge means;
said capillary tube purge means including purge block means having a first opening sized to sealingly receive a portion of a capillary tube and second inlet means adapted to receive a means for injecting a purge liquid;
said second inlet means and first opening being joined and containing continuous walls with no outlet openings to the flow of fluid whereby fluid injected in said purge means is applied directly to said capillary column means to purge said column.

10. Apparatus according to claim 9 in which said electrophoresis tube purge means includes means for supplying electrophoretic medium to said capillary tube.

11. Apparatus for detecting bands in a capillary tube having a predetermined direction of motion in a separation medium within the capillary tube comprising:
a capillary tube adapted to contain a separating medium;
means for applying an electrophoresis separation electrical potential across said capillary tube;
a detector means incorporating a detection volume not larger than 100 nanoliters;
said detector means including means for removably holding the capillary tube within the detector;
said capillary tube having a diameter no greater than 700 micrometers;
split-flow means for injecting samples into said tube;
said split flow means incorporating high voltage isolating means and injection block means;
said injection block means having a first inlet means to receive a predetermined amount of sample;
said injection block means further including a means for dividing the sample applied to the inlet in a precise ratio with one conduit means receiving a predetermined proportion of sample not supplied to said capillary tube and a capillary tube recepticle for applying a predetermined amount of sample to said capillary tube;
said split flow means further including a common junction between said first inlet means, conduit means and capillary recepticle;
said capillary recepticle including inlet means for receiving a portion of a capillary tube;
said inlet means for receiving a portion of a capillary tube communicating with said common junction means, whereby a portion of the sample applied to said common junction means enters said capillary tube means and another portion is transmitted through said conduit means;
an inlet moving mechanism;
said capillary tube mounted on said inlet moving mechanism adjustable to move the capillary tube from the said capillary tube outlet means to the said means for applying an electrophoresis separation electrical potential;
an electromigration voltage connector leading to a supply of electromigration sample introduction voltage and mounted on the said inlet moving mechanism;
an electromigration electrode communicating with the said common junction with the injection block;
said electromigration electrode having an electrode contact outside of the injection block; and
said electromigration voltage connector in electrical contact with the said electrode contact when the said inlet moving mechanism positions the capillary tube in the said capillary inlet tube means.

12. Apparatus for detecting bands in a capillary tube having a predetermined direction of motion in a separation medium within the capillary tube comprising:
- a capillary tube adapted to contain a separating medium;
- means for applying an electrophoresis separation electrical potential across said capillary tube;
- detector means incorporating a detection volume not larger than 100 nanoliters;
- said detector means including means for removably holding the capillary tube within the detector;
- said capillary tube having a diameter no greater than 700 micrometers;
- split-flow means for injecting samples into said tube;
- said split flow means incorporating high voltage isolating means; and
- injection block purge means, said injection block purge means including a second purge conduit means and means for closing said capillary tube inlet means whereby purge fluid may flow into said purge conduit means while said conduit means and electrophoresis tube means are sealed.

13. Apparatus according to claim 12 further including:
- a capillary tube purge means;
- said capillary tube purge means including purge block means having a first opening sized to sealingly receive a portion of a capillary tube and second inlet means adapted to receive a means for injecting a purge liquid;
- said second inlet means and first opening being joined and containing continuous walls with no outlet openings to the flow of fluid whereby fluid injected in said purge means is applied directly to said capillary column means to purge said column.

14. Apparatus according to claim 13 in which said electrophoresis tube purge means includes means for supplying electrophoretic medium to said capillary tube.

15. Apparatus in accordance with claim 14 in which said split flow means further includes a common junction between said first inlet means, conduit means and capillary recepticle;
- said capillary recepticle including inlet means for receiving a portion of a capillary tube; and
- said inlet means for receiving a portion of a capillary tube communicating with said common junction means, whereby a portion of the sample applied to said common junction means enters said capillary tube means and another portion is transmitted through said conduit means.

16. Apparatus for detecting bands in a capillary tube having a predetermined direction of motion in a separation medium within the capillary tube comprising:
- a capillary tube adapted to contain a separating medium;
- means for applying an electrophoresis separation electrical potential across said capillary tube;
- detector means incorporating a detection volume not larger than 100 nanoliters;
- said detector means including means for removably holding the capillary tube within the detector;
- said capillary tube having a diameter no greater than 700 micrometers;
- split-flow means for injecting samples into said tube;
- said split flow means incorporating high voltage isolating means; and
- a capillary tube purge means;
- said capillary tube purge means including purge block means having a first opening sized to sealingly receive a portion of a capillary tube and second inlet means adapted to receive a means for injecting a purge liquid;
- said second inlet means and first opening being joined and containing continuous walls with no outlet openings to the flow of fluid whereby fluid injected in said purge means is applied directly to said capillary column means to purge said column.

17. Apparatus according to claim 16 in which said electrophoresis tube purge means includes means for supplying electrophoretic medium to said capillary tube.

18. Apparatus in accordance with claim 17 in which said split flow means further includes a common junction between said first inlet means, conduit means and capillary recepticle;
- said capillary recepticle including inlet means for receiving a portion of a capillary tube; and
- said inlet means for receiving a portion of a capillary tube communicating with said common junction means, whereby a portion of the sample applied to said common junction means enters said capillary tube means and another portion is transmitted through said conduit means.

19. Apparatus according to claim 18 in which said electrophoresis tube purse means includes means for supplying electrophoretic medium to said capillary tube.

20. Apparatus in accordance with claim 19 in which said split flow means further includes a common junction between said first inlet means, conduit means and capillary recepticle;
- said capillary recepticle including inlet means for receiving a portion of a capillary tube; and
- said inlet means for receiving a portion of a capillary tube communicating with said common junction means, whereby a portion of the sample applied to said common junction means enters said capillary tube means and another portion is transmitted through said conduit means.

21. A method for detecting bands in a capillary tube comprising the steps of:
- injecting a sample into said capillary tube through a split flow injection block;
- applying voltage across the capillary tube;
- transmitting light through a first aperture, said capillary tube, a second aperture and a light sensor in that order wherein said second aperture has a width no greater than twice the diameter of the separating medium and is transverse thereto, and the illuminated detection volume inside the said capillary tube is not greater than 100 nanoliters;
- the step of injecting a sample including the steps of: injecting sample into a first inlet of the injection block means to apply a predetermined amount of sample; and dividing the sample in the injection block means between a conduit means for receiving a predetermined amount of sample not supplied to said capillary tube and a capillary tube; and
- purging said injection block means by applying a purge liquid to a second purge conduit means and closing said capillary tube inlet means whereby purge fluid may flow into said purge conduit means while said conduit means and electrophoresis tube means are sealed.

22. A method according to claim 21 further including the steps of inserting said capillary tube into a purge means having a purge block means with a first opening sized to sealingly receive a portion of a capillary tube and second inlet means being adapted to receive a means for injecting a purge liquid; but containing walls with no openings to the flow of fluid;

injecting fluid in said purge means wherein it flow directly to said capillary tube means to purge said tube.

23. A method according to claim 21 further including the steps of inserting said capillary tube into a purge means having a purge block means with a first opening sized to sealingly receive a portion of a capillary tube and second inlet means being adapted to receive a means for injecting a purge liquid; but containing walls with no openings to the flow of fluid;

injecting fluid in said purge means wherein it flows directly to said capillary tube means to purge said tube.

24. A method for detecting bands in a capillary tube comprising the steps of:

injecting a sample into said capillary tube through a split flow injection block;

applying voltage across the capillary tube;

transmitting light through a first aperture, said capillary tube, a second aperture and a light sensor in that order wherein said second aperture has a width no greater than twice the diameter of the separating medium and is transverse thereto, and the illuminated detection volume inside the said capillary tube is not greater than 100 nanoliters; and purging said injection block means by applying a purge liquid to a second purge conduit means and closing said capillary tube inlet means whereby purge fluid may flow into said purge conduit means while said conduit means and electrophoresis tube means are sealed.

25. A method for detecting bands in a capillary tube comprising the steps of:

injecting a sample into said capillary tube through a split flow injection block;

applying voltage across the capillary tube;

transmitting light through a first aperture, said capillary tube, a second aperture and a light sensor in that order wherein said second aperture has a width no greater than twice the diameter of the separating medium and is transverse thereto, and the illuminated detection volume inside the said capillary tube is not greater than 100 nanoliters;

inserting said capillary tube into a purge means having a purge block means with a first opening sized to sealingly receive a portion of a capillary tube and second inlet means being adapted to receive a means for injecting a purge liquid; but containing walls with no openings to the flow of fluid; and injecting fluid in said purge means wherein it flows directly to said capillary tube means to purge said tube.

26. Apparatus for detecting bands in a capillary tube having a predetermined direction of motion in a separation medium within the capillary tube comprising:

a capillary tube adapted to contain a separating medium;

means for applying an electrical potential across said capillary tube;

flow cell means for detecting bands;

split-flow means for injecting samples into said tube;

said split flow means incorporating fluid switching means and high voltage switching means;

injection block means;

said injection block means having a first inlet means to receive a predetermined amount of sample;

said injection block means further including means for dividing the sample applied to the inlet in a precise ratio with one conduit means receiving a predetermined proportion of sample not supplied to said capillary tube and a capillary tube recepticle for applying a predetermined amount of sample to said capillary tube;

said split flow means further including a common junction between said first inlet means, conduit means and capillary recepticle;

said capillary recepticle including inlet means for receiving a portion of a capillary tube;

said inlet means for receiving a portion of a capillary tube communicating with said common junction means, whereby a portion of the sample applied to said common junction means enters said capillary tube means and another portion is transmitted through said conduit means; and injection block purge means, said injection block purge means including a second purge conduit means and means for closing said capillary tube inlet means whereby purge fluid may flow into said purge conduit means while said conduit means and electrophoresis tube means are sealed.

27. Apparatus according to claim 26 further including:

a capillary tube purge means;

said capillary tube purge means including purge block means having a first opening sized to sealingly receive a portion of a capillary tube and second inlet means adapted to receive a means for injecting a purge liquid;

said second inlet means and first opening being joined and containing continuous walls with no outlet openings to the flow of fluid whereby fluid injected in said purge means is applied directly to said capillary column means to purge said column.

28. Apparatus according to claim 27 in which said electrophoresis tube purge means includes means for supplying electrophoretic medium to said capillary tube.

29. Apparatus for detecting bands in a capillary tube having a predetermined direction of motion in a separation medium within the capillary tube comprising:

a capillary tube adapted to contain a separating medium;

means for applying an electrical potential across said capillary tube;

flow cell means for detecting bands;

split-flow means for injecting samples into said tube;

said split flow means incorporating fluid switching means and high voltage switching means;

injection block means;

said injection block means having a first inlet means to receive a predetermined amount of sample;

said injection block means further including a means for dividing the sample applied to the inlet in a precise ratio with one conduit means receiving a predetermined proportion of sample not supplied to said capillary tube and a capillary tube recepticle for applying a predetermined amount of sample to said capillary tube; and injection block purge means, said injection block purge means including a second purge conduit means and means for closing said capillary tube inlet means whereby purge fluid may flow into said purge conduit means while said conduit means and electrophoresis tube means are sealed.

30. Apparatus according to claim 29 further including:
a capillary tube purge means;
said capillary tube purge means including purge block means having a first opening sized to sealingly receive a portion of a capillary tube and second inlet means adapted to receive a means for injecting a purge liquid;
said second inlet means and first opening being joined and containing continuous walls with no outlet openings to the flow of fluid whereby fluid injected in said purge means is applied directly to said capillary column means to purge said column.

31. Apparatus according to claim 30 in which said electrophoresis tube purge means includes means for supplying electrophoretic medium to said capillary tube.

32. Apparatus for detecting bands in a capillary tube having a predetermined direction of motion in a separation medium within the capillary tube comprising:
a capillary tube adapted to contain a separating medium;
means for applying an electrical potential across said capillary tube;
flow cell means for detecting bands;
split-flow means for injecting samples into said tube;
said split flow means incorporating fluid switching means and high voltage switching means;
injection block means;
said injection block means having a first inlet means to receive a predetermined amount of sample;
said injection block means further including a means for dividing the sample applied to the inlet in a precise ratio with one conduit means receiving a predetermined proportion of sample not supplied to said capillary tube and a capillary tube recepticle for applying a predetermined amount of sample to said capillary tube; and
including injection block purge means, said injection block purge means including a second purge conduit means and means for closing said capillary tube inlet means whereby purge fluid may flow into said purge conduit means while said conduit means and electrophoresis tube means are sealed.

33. Apparatus for detecting bands in a capillary tube having a predetermined direction of motion in a separation medium within the capillary tube comprising:
a capillary tube adapted to contain a separating medium;
means for applying an electrical potential across said capillary tube;
flow cell means for detecting bands;
split-flow means for injecting samples into said tube;
said split flow means incorporating fluid switching means and high voltage switching means;
injection block means;
said injection block means having a first inlet means to receive a predetermined amount of sample;
said injection block means further including a means for dividing the sample applied to the inlet in a precise ratio with one conduit means receiving a predetermined proportion of sample not supplied to said capillary tube and a capillary tube recepticle for applying a predetermined amount of sample to said capillary tube;
injection block purge means, said injection block purge means including a second purge conduit means and means for closing said capillary tube inlet means whereby purge fluid may flow into said purge conduit means while said conduit means and electrophoresis tube means are sealed; and
a capillary tube purge means;
said capillary tube purge means including purge block means having a first opening sized to sealingly receive a portion of a capillary tube and second inlet means adapted to receive a means for injecting a purge liquid;
said second inlet means first opening being joined and containing continuous walls with no outlet openings to the flow of fluid whereby fluid injected in said purge means is applied directly to said capillary column means to purge said column.

34. Apparatus according to claim 33 in which said electrophoresis tube purge means includes means for supplying electrophoretic medium to said capillary tube.

35. Apparatus for detecting bands in a capillary tube having a predetermined direction of motion in a separation medium within the capillary tube comprising:
a capillary tube adapted to contain a separating medium;
means for applying an electrical potential across said capillary tube;
flow cell means for detecting bands;
split-flow means for injecting samples into said tube;
said split flow means incorporating fluid switching means and high voltage switching means;
injection block means;
said injection block means having a first inlet means to receive a predetermined amount of sample;
said injection block means further including means for dividing the sample applied to the inlet in a precise ratio with one conduit means receiving a predetermined proportion of sample not supplied to said capillary tube and a capillary tube recepticle for applying a predetermined amount of sample to said capillary tube;
said split flow means further including a common junction between said first inlet means, conduit means and capillary recepticle;
said capillary recepticle including inlet means for receiving a portion of a capillary tube; and
said inlet means for receiving a portion of a capillary tube communicating with said common junction means, whereby a portion of the sample applied to said common junction means enters said capillary tube means and another portion is transmitted through said conduit means; and
a capillary tube purge means;
said capillary tube purge means including purge block means having a first opening sized to sealingly receive a portion of a capillary tube and second inlet means adapted to receive a means for injecting a purge liquid;
said second inlet means and first opening being joined and containing continuous walls with no outlet openings to the flow of fluid whereby fluid injected in said purge means is applied directly to said capillary column means to purge said column.

36. Apparatus according to claim 35 in which said electrophoresis tube purge means includes means for supplying electrophoretic medium to said capillary tube.

37. A method of electrophoresis comprising the steps of:
   injecting sample into the end of capillary tube through a split flow block;
   switching the end of the capillary tube containing the sample from the point of injection at the split flow block to a source of buffer at high electrical potential;
   electrophoresing the sample; and
   detecting the electrophoretically separated bands in a flow cell;
   the step of injecting a sample including the steps of: injecting sample into a first inlet of the injection block means to apply a predetermined amount of sample; and dividing the sample in the injection block means between a conduit means for receiving a predetermined amount of sample not supplied to said capillary tube and a capillary tube; and
   purging said injection block means by applying a purge liquid to a second purge conduit means and closing said capillary tube inlet means whereby purge fluid may flow into said purge conduit means while said conduit means and electrophoresis tube means are sealed.

38. A method according to claim 37 further including the steps of:
   inserting said capillary tube into a purge means having a purge block means with a first opening sized to sealingly receive a portion of a capillary tube and second inlet means being adapted to receive a means for injecting a purge liquid but containing walls with no openings to the flow of fluid; and
   injecting fluid in said purge means wherein it flows directly to said capillary tube means to purge said tube.

39. A method of electrophoresis comprising the steps of:
   injecting sample into the end of capillary tube through a split flow block;
   switching the end of the capillary tube containing the sample from the point of injection at the split flow block to a source of buffer at high electrical potential;
   electrophoresing the sample;
   detecting the electrophoretically separated bands in a flow cell; and
   purging said injection block means by applying a purge liquid to a second purge conduit means and closing said capillary tube inlet means whereby purge fluid may flow into said purge conduit means while said conduit means and electrophoresis tube means are sealed.

40. A method according to claim 39 further including the steps of:
   inserting said capillary tube into a purge means having a purge block means with a first opening sized to sealingly receive a portion of a capillary tube and second inlet means being adapted to receive a means for injecting a purge liquid but containing walls with no openings to the flow of fluid;
   injecting fluid in said purge means wherein it flows directly to said capillary tube means to purge said tube.

41. Apparatus for detecting bands in a capillary tube having a predetermined direction of motion in a separation medium within the capillary tube comprising:
   a capillary tube adapted to contain a separating medium;
   means for applying an electrophoresis separation electrical potential across said capillary tube;
   detector means incorporating a detection volume not larger than 100 nanoliters;
   said detector means including means for removably holding the capillary tube within the detector;
   said syringe port being sized to tightly receive a syringe needle;
   means for applying an electric potential to said junction; and
   a flush opening communicating with said junction.

* * * * *